United States Patent
Li et al.

(10) Patent No.: US 8,756,982 B2
(45) Date of Patent: Jun. 24, 2014

(54) METHOD AND DEVICE FOR MEASURING BY PENETROMETRY AN INTERFACE OR SURFACE TENSION OF AN INTERFACE BETWEEN TWO FLUIDS

(75) Inventors: Huai Zhi Li, Heillecourt (FR); Nicolas Dietrich, Toulouse (FR)

(73) Assignee: Universite de Lorraine, Nancy Cedex (FR)

( * ) Notice: Subject to any disclaimer, the term of this patent is extended or adjusted under 35 U.S.C. 154(b) by 201 days.

(21) Appl. No.: 13/499,478

(22) PCT Filed: Sep. 28, 2010

(86) PCT No.: PCT/FR2010/052030
§ 371 (c)(1),
(2), (4) Date: Jun. 18, 2012

(87) PCT Pub. No.: WO2011/039461
PCT Pub. Date: Apr. 7, 2011

(65) Prior Publication Data
US 2012/0186357 A1    Jul. 26, 2012

(30) Foreign Application Priority Data
Oct. 1, 2009 (FR) .................................. 09 56828

(51) Int. Cl.
*G01N 13/00* (2006.01)
(52) U.S. Cl.
USPC ......................................... 73/64.48; 73/64.49
(58) Field of Classification Search
CPC .......... G01N 13/02; G01N 2013/0283; G01N 2013/02; G01N 2013/0241; G01N 2013/0291
USPC .................. 73/64.48, 64.49, 64.51, 64.52
See application file for complete search history.

(56) References Cited

U.S. PATENT DOCUMENTS

| | | | |
|---|---|---|---|
| 4,644,782 A | 2/1987 | Joseph | |
| 4,953,389 A | 9/1990 | Schurch | |
| 5,542,289 A * | 8/1996 | Hool et al. | 73/64.52 |
| 5,824,887 A * | 10/1998 | Baumlin et al. | 73/64.48 |
| 2004/0070360 A1 | 4/2004 | Schulz et al. | |
| 2009/0320568 A1* | 12/2009 | Desie et al. | 73/64.52 |
| 2010/0188662 A1* | 7/2010 | Saito et al. | 356/445 |

FOREIGN PATENT DOCUMENTS

EP    1950550 A1    7/2008

OTHER PUBLICATIONS

Lieberman et al. "Use of a cone penetrometer deployed video-imaging system for in situ detection of NAPLs in subsurface soil environments". <http://info.ngwa.org/GWOL/pdf/982664613.PDF>.*

(Continued)

*Primary Examiner* — Lisa Caputo
*Assistant Examiner* — Jonathan Dunlap
(74) *Attorney, Agent, or Firm* — Egbert Law Offices, PLLC

(57) ABSTRACT

A method is provided for measuring an interfacial tension ($\sigma$) for liquid-liquid interfaces or surface tension for liquid-gas interfaces. The method is characterized in that the measurement is carried out by the penetrometry of an interface between two fluids of a sample in a pipe comprising at least one window made of a transparent material, using a rod moving at constant speed orthogonally to the interface, a profile of the interface being deformed by the penetration of the rod and a series of images of the profile being captured in real time by an image-capturing system during the deformation and the crossing of the interface. A device for implementing the method is also disclosed.

12 Claims, 1 Drawing Sheet

(56) References Cited

OTHER PUBLICATIONS

ASTM D 217-02. "Standard Test Methods for Cone Penetration of Lubrication Grease". 2002. <http://www.shxf17.com/pdf/ASTMD217-02.pdf>.*

Lauda, Dr. R. Wobser GMBG & Co. TD 3. <http://www.lauda-brinkmann.com/downloads/Flyer_TD3_E_web.pdf>.*

DirectIndustry.com. "Tensiometer for surface and interfacial tension measurement". Available online May 4, 2009. <http://www.directindustry.com/prod/lauda/tensiometer-for-surface-and-interfacial-tension-measurement-23650-380928.html>.*

International Search Report for corresponding International Application No. PCT/FR2010/052030.

* cited by examiner

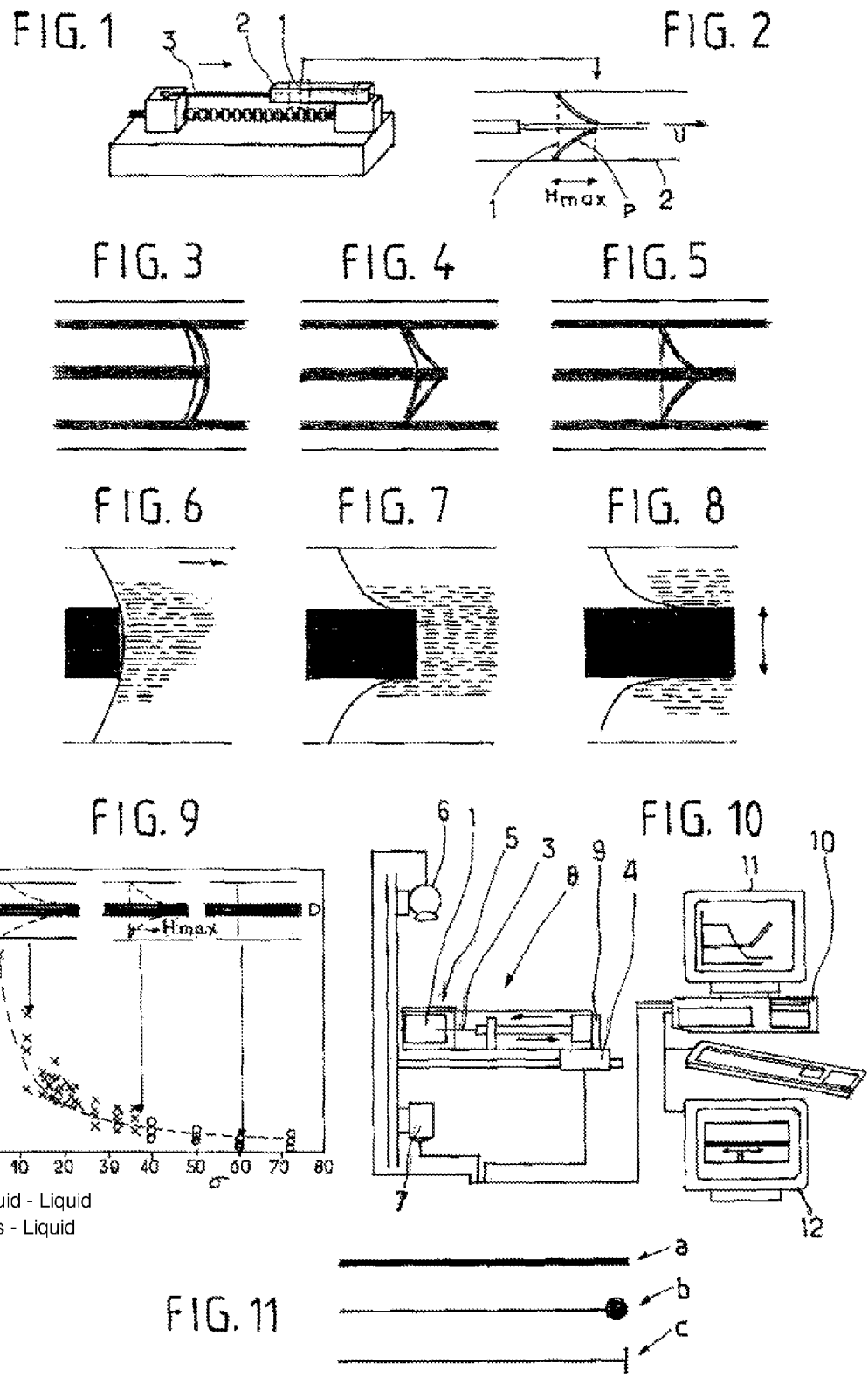

METHOD AND DEVICE FOR MEASURING BY PENETROMETRY AN INTERFACE OR SURFACE TENSION OF AN INTERFACE BETWEEN TWO FLUIDS

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention concerns a method of measuring the surface or interface tension between two fluids and a device for implementing the method.

2. Description of Related Art Including Information Disclosed Under 37 CFR 1.97 and 37 CFR 1.98.

The tension measured is referred to as "surface tension" for a gas-liquid system and is referred to as "interface tension" for a liquid-liquid system.

The invention can be applied in numerous economic fields, for example for producing cosmetics, detergents, pharmaceutical or chemical products, measuring apparatus in public or private research laboratories, in higher education for practical work and in general terms in all sectors that require to define the fundamental properties of a liquid-liquid or liquid-gas interface, such as rigidity, visco-elasticity, deformability, etc.

Numerous techniques for measuring the interface tension between fluids are already known, such as for example:
- measurements by visualisation (for example the hanging drop technique)
- tensile force measurements by Wilhelmy plate or by Du Noüy ring on a plate
- measurements based on Rayleigh instability such as the oscillating jet technique, or on the change in polarisation of the electromagnetic waves at the interface, this is the ellipsometry technique.

Some techniques are based on the Laplace equation for calculating the droplet volume and the maximum bubble pressure. These techniques use digitisation and computer processing such as the drop profile, the bubble profile and even the microfluid tool.

Unfortunately these techniques, through their use of a large sample of fluid and through the size of the devices, prevent measurement at high temperatures. Moreover, the liquid medium must often be transparent. In particular these techniques do not apply or are too imprecise in the case of viscous and/or elastic liquids.

To remedy these drawbacks, the invention proposes a novel microscopic technique of measuring surface or interface tension making it possible to measure this quantity with precision at high temperatures (above 50° C.) and aims it the following objectives:
- rapidly measuring the interface and surface tension,
- requiring very little fluid for making the measurement,
- allowing heating of the microsystem for achieving high temperatures,
- applying to an opaque and/or viscous liquid.

The objectives in use referred to above are highly advantageous for applications where liquids have high added values or have solid phases at ambient temperature (cosmetics, pharmaceutics, petrochemicals, etc.).

BRIEF SUMMARY OF THE INVENTION

All these objectives are achieved by the invention, which consists of a method of measuring an interface tension ($\sigma$) for liquid-liquid interfaces or surface tension for liquid-gas interfaces, characterised in that the measurement is made by penetrometry of an interface between two fluids of a sample contained in a conduit comprising at least one window made from transparent material, at least one rod moved at constant speed and orthogonally to the interface, a profile (P) of the interface being deformed by the penetration of the rod and a series of images of the profile (P) being acquired in real time by an image-taking system during the deformation and traversing of the interface.

The invention proposes two preferential formulations for deriving the tension ($\sigma$) from the analysis of the deformation of the profile.

The invention also concerns a machine for implementing a method of measuring an interface tension ($\sigma$) for liquid-liquid interfaces or surface tension for liquid-gas interfaces, characterised in that it comprises at least the following essential means:
- a conduit with at least one transparent window and containing a measurement sample composed of two fluids separated by an interface,
- a rod moved at speed in a direction orthogonal to the interface, the said rod being caused to deform and then pass through the interface at the centre thereof,
- an image-taking means for acquiring a series of digital images of the profile of the interface during deformation thereof.

Preferentially, the machine comprises a means of raising the conduit to a predetermined constant temperature and maintaining it thereat, which is for example a Peltier module. It also preferably comprises a light source for illuminating the interface.

BRIEF DESCRIPTION OF THE SEVERAL VIEWS OF THE DRAWINGS

The invention will be understood better from a reading of the description given below with reference to the accompanying figures:

FIG. 1 is outline diagram of a device according to the invention,

FIG. 2 is a detail view of the interface,

FIGS. 3 to 5 are diagrams displaying the form of the interface during a measurement, FIGS. 6 to 8 show validation of the velocity fields within the fluids during a measurement, FIG. 9 is curve for the change in the deformation of the interface as a function of the interface tension for the device in FIG. 1 and at 25° C., FIG. 10 is a schematic diagram of a device for implementing the invention, FIG. 11 shows a variant of rod ends.

DETAILED DESCRIPTION OF THE INVENTION

According to the principle of the invention, an interface tension (σ) (for liquid-liquid interfaces) or surface tension (for liquid-gas interfaces) is measured by the penetrometry method for an interface (1) under the following conditions:

An initially vertical interface (1) between two liquids, or horizontal between a liquid and air, is produced in a conduit (2) (for example with a square cross-section of dimensions 5 mm*5 mm*10 cm) (see FIG. 1). For a conduit with a large cross-section, the conduit should be vertical. On the other hand, capillarity phenomena make it possible to keep a liquid-liquid interface vertical in a horizontal conduit.

A rod (3) with a millimetric or sub-millimetric diameter is moved by any means, for example a motor (4). It moves at constant speed and orthogonally to the surface or to the surface element with which it is in contact, and is caused to deform and then pass through the liquid-liquid or gas-liquid interface (1) preferentially at its centre. It is possible to orient the conduit horizontally or vertically as soon as the rod passes through the interface orthogonally, and hence the flexibility of the method.

The profile (P) of the interface deformed by the penetration of the rod is analysed by a camera (7) in real time (see FIGS. 2 to 8).

The interface tension (σ) is derived from the image analysis made at the time of rupture of the interface. This deformation is related to the value of the interface tension.

FIG. 9 shows the change at 25° C. in the deformation distance $H_{max}$ as a function of the interface tension for liquid-liquid systems or gas-liquid systems. A first approach makes it possible to assess the value of the interface tension rapidly with a difference of 20% compared with conventional techniques:

$$\frac{H_{max}}{D} = \frac{2.2}{\sigma}$$

for the case of the diameter of the rod $D=7.10^{-4}$ m.
D diameter of the rod, m
$H_{max}$: maximum height, m
σ: surface or interface tension, mN/m By refining their study, the inventors have arrived at a much more precise (2% difference) and more general law, by means of the following novel formula:

$$\sigma = 59.28 \left(\frac{D}{H_{max}}\right)^{1/2} U^{1/8}$$

U: speed of the rod, mm/s
D: diameter of the rod, m
$H_{max}$: maximum height, m
σ: surface or interface tension, mN/m Thus knowledge of Hmax makes it possible to directly access the interface tension with very great precision.

A device for implementing this measurement principle is now described in detail (see FIG. 10), given by way of non-limitative example embodiment.

The interface (1) is deformed by a rod (3) connected to a movement member controlled by a motor (4). The conduit (2) is thermostatically controlled by a Peltier module (5) (heat pump which—by virtue of a change in polarity—can equally well be used to heating or cooling) or by a technically equivalent means.

The conduit (2) is made from glass with a square cross-section (5 mm*5 mm*10 cm) with a wall connected to the Peltier module. The rod (3) is made from a rigid metal and has a diameter of less than 1 mm, and preferably between 500 mm and 1500 mm.

A light source (6) illuminates the interface and is an integrating sphere in order to provide homogeneous luminosity in all directions in space. This design ensures uniform illumination of the interface (1) and gives a constant contrast of the image of its contour with respect to a background.

The lens of the camera used is of a telecentric type. Thus the magnification of the optical system does not depend on the distance from the lens to the interface and optical calibration can be carried out once and for all, whereas with any other type of lens it would be necessary to do it again before carrying out any measurement. It has very low distortion. This design consequently offers very great user friendliness and flexibility in use of the apparatus while giving the greatest precision on the measurements of the interface and surface tension.

The camera chosen (7) is of the CCD type and compliant with the CCIT standard, and analyses 25 images per second with a format of 640×512 pixels.

The speed of movement of the rod is preferably adjustable, for example from 1 to 20 mm/s, in correlation with the speed of photographing.

A control box (8) contains a controller controlling the temperature of the Pelletier module (5) (programmable PID controller), a force sensor (9) connected to the moving member, a speed regulator for the moving member, and buttons affording manual control of the moving member making it possible to control its movement manually if necessary, without passing through the computer.

The whole of the tensimeter is controlled from a PC-compatible microcomputer (10). The latter is equipped with a rapid video acquisition card, a motor control card and an acquisition card for the force sensor and thermocouple and comprises control screens (11, 12).

Software provides all the operations of adjustment of the tensimeter (calibration of sensors, parameterising of image processing, etc.), and data acquisition and processing.

Variant embodiments of the method are possible, and in particular variants can be provided concerning:

the cross-section of the conduit, which is not necessary square;
the form or the profile of the end of the rod, by way of example FIG. 11 shows a cylindrical rod (a), a ball end (b), a disc end (c);
the material of the conduit. It is possible to use a conduit made from non-transparent material but comprising two transparent windows, one to allow illumination of the interface, the other to allow photographing. In addition, if the conduit is cylindrical or non-planar, the said windows will be flat;
the material of the rod. It may be advantageous to use hydrophobic or hydrophilic materials or ones having other characteristics according to the nature of the fluids present;
the real-time photographic system, which may be a camera or a photographic apparatus.

The advantages of the invention are in particular as follows:
- the possibility of using a low volume of fluid to be tested during a measurement: less than 1 ml with the invention, whereas it is around 10 to 50 ml with the known measuring appliances. This is particularly advantageous for high-priced fluids to be tested, the volumes of the two fluids contained in the conduit not necessarily being identical;
- the possibility of heating or cooling the measurement conduit or the sample because of its small bulk and its accessibility. In existing appliances, it is difficult to add refrigeration or heating means;
- the possibility of making the measurement on media for which measurement was impossible with conventional techniques. For example, the water drop technique is not applicable with highly viscous liquids whereas the technique according to the invention is applicable thereto;
- the possibility of making the measurement with good precision within a wide range of temperatures from −10° C. to 100° C. (for example), which was not permitted by the prior techniques;
- the possibility of validating and visualising the velocity fields of the fluids in real time, by associating with the device an apparatus known by the name micro-PIV (particle image velocimetry) that gives images of the velocity fields, in a longitudinal plane of the conduit, such as those presented in FIGS. 6 to 8 by way of example. These images have an advantage in showing the influence of the viscosity of the fluid when the interface is deformed;
- flexibility of the device: it can be oriented horizontally or vertically so long as the rod passes through the interface orthogonally. For a conduit with a large cross-section, the conduit must be vertical. On the other hand, capillarity phenomena make it possible to keep a liquid-liquid interface vertical in a horizontal conduit.

We claim:

1. A method for measuring an interface tension for a liquid-liquid interface or a surface tension for a liquid-gas interface, the method comprising:
   - measuring the interface between two fluids of a sample contained in a conduit by using a penetrometer, said conduit having at least one window formed of a transparent material;
   - moving at least one rod at a constant speed within said conduit orthogonal to the interface;
   - deforming a profile of the interface by the movement of the rod; and
   - acquiring a series of images of the profile in real time by an image-taking system during the deforming and traversing of the interface.

2. The method of claim 1, further comprising:
   analyzing the series of images of the profile; and
   assessing the tension by applying a formula of $$\frac{H_{max}}{D} = \frac{2.2}{\sigma}$$

in which said rod has a diameter of $D=7.10^{-4}$ m., in which $H_{max}$ is a maximum height (m), and in which $\sigma$ is the surface tension or the interface tension (mN/m).

3. The method of claim 1, further comprising:
   analyzing the series of images of the profile; and
   assessing the tension by applying a formula of $$\sigma = 59.28 \left(\frac{D}{H_{max}}\right)^{1/2} U^{1/8}$$

where U is a speed of said rod (mm/s), D is a diameter of said rod (m), $H_{max}$ is a maximum height (m), and $\sigma$ is the surface tension or the interface tension (mN/m).

4. An apparatus for measuring an interface tension for a liquid-liquid interface or a surface tension for a liquid-gas interface, the apparatus essentially comprising:
   - a conduit having at least one transparent window, said conduit containing a measurement sample having two fluids separated by the interface, the interface located within said conduit;
   - a rod movable within and along said conduit in a direction orthogonal to the interface such that said rod deforms the interface and passes through the interface;
   - an image-taking means for acquiring a series of digital images of a profile of the interface during the deforming of the interface.

5. The apparatus of claim 4, further comprising:
   a means for taking said conduit to a constant temperature and for maintaining said conduit at the constant temperature.

6. The apparatus of claim 5, the means for taking said conduit to a constant temperature being a Peltier module.

7. The apparatus of claim 4, further comprising:
   a light source positioned so as to illuminate the interface.

8. The apparatus of claim 4, said rod having a diameter of less than 1 millimeter.

9. The apparatus of claim 8, said diameter of said rod being between 500 mm and 1500 mm.

10. The apparatus of claim 4, said conduit having a square cross-section.

11. The apparatus of claim 4, said measurement sample having a volume of no more than one millimeter.

12. The apparatus of claim 4, said image-taking means having a telecentric lens.

* * * * *